United States Patent
Rothmann et al.

(10) Patent No.: US 8,937,174 B2
(45) Date of Patent: Jan. 20, 2015

(54) METHOD AND DEVICE FOR THE AUTOMATED PROCESSING OF A SAMPLE

(75) Inventors: Thomas Rothmann, Langenfeld (DE); Ralf Himmelreich, Langenfeld (DE); Thomas Laue, Elsdorf (DE)

(73) Assignee: Qiagen GmbH, Hilden (DE)

( * ) Notice: Subject to any disclaimer, the term of this patent is extended or adjusted under 35 U.S.C. 154(b) by 845 days.

(21) Appl. No.: 12/864,641

(22) PCT Filed: Jan. 13, 2009

(86) PCT No.: PCT/EP2009/050285
§ 371 (c)(1),
(2), (4) Date: Dec. 8, 2011

(87) PCT Pub. No.: WO2009/098104
PCT Pub. Date: Aug. 13, 2009

(65) Prior Publication Data
US 2012/0070823 A1 Mar. 22, 2012

(30) Foreign Application Priority Data
Feb. 7, 2008 (EP) .................................... 08151152

(51) Int. Cl.
*C07H 21/00* (2006.01)
*C12Q 1/68* (2006.01)
*C12M 1/00* (2006.01)
*B01L 3/00* (2006.01)
*B01L 7/00* (2006.01)

(52) U.S. Cl.
CPC .......... *B01L 3/502715* (2013.01); *C12M 47/06* (2013.01); *B01J 2219/00335* (2013.01); *B01J 2219/00373* (2013.01); *B01J 2219/00423* (2013.01); *B01J 2219/00605* (2013.01); *B01J 2219/00641* (2013.01); *B01J 2219/00722* (2013.01); *B01L 7/52* (2013.01); *B01L 2200/025* (2013.01); *B01L 2200/027* (2013.01); *B01L 2200/10* (2013.01); *B01L 2300/0672* (2013.01);
(Continued)

(58) Field of Classification Search
None
See application file for complete search history.

(56) References Cited

U.S. PATENT DOCUMENTS

| | | | |
|---|---|---|---|
| 6,706,519 B1 * | 3/2004 | Kellogg et al. | 435/287.2 |
| 2003/0027203 A1 * | 2/2003 | Fields | 435/6 |

(Continued)

FOREIGN PATENT DOCUMENTS

| | | |
|---|---|---|
| WO | 2005/049206 | 6/2005 |
| WO | 2006042838 | 4/2006 |

OTHER PUBLICATIONS

International Preliminary Report on Patentability (German and English) PCT/EP2009/050285 dated Jan. 13, 2009 (12 pages).
(Continued)

*Primary Examiner* — Robert T Crow
*Assistant Examiner* — Joseph G Dauner
(74) *Attorney, Agent, or Firm* — Miles & Stockbridge, PC (57) ABSTRACT

The invention relates to a method and a device for the automatic processing of biological samples which can have a relatively large volume and which can be further processed by a microfluidic system. A container is provided with a filter and can be or is closed. A biological sample is introduced into the container. An inlet or outlet for liquids is mounted downstream of the filter. In order to carry out processing, liquids that are present in the container are not only sucked off through the filter and passed on via the inlet or outlet, but liquids required for processing are also pumped into the container through the filter. The container can be connected to a microfluidic system in a relatively easy manner since only one conduit is required for an automated processing.

17 Claims, 6 Drawing Sheets

(52) U.S. Cl.
CPC .. *B01L 2300/0681* (2013.01); *B01L 2300/0816* (2013.01); *B01L 2300/1827* (2013.01)
USPC ........................ 536/25.4; 435/6.1; 435/283.1

(56) References Cited

U.S. PATENT DOCUMENTS

| 2003/0134416 | A1* | 7/2003 | Yamanishi et al. | ............ | 435/372 |
| 2004/0086872 | A1* | 5/2004 | Childers et al. | ................... | 435/6 |
| 2004/0229349 | A1 | 11/2004 | Daridon | | |
| 2007/0048194 | A1 | 3/2007 | Schulein et al. | | |
| 2007/0202536 | A1* | 8/2007 | Yamanishi et al. | ............ | 435/7.1 |
| 2007/0248958 | A1* | 10/2007 | Jovanovich et al. | .............. | 435/6 |

OTHER PUBLICATIONS

International Search Report of PCT/EP2009/050285 dated May 12, 2009 (6 pages).

* cited by examiner

METHOD AND DEVICE FOR THE AUTOMATED PROCESSING OF A SAMPLE

CROSS REFERENCE TO RELATED APPLICATIONS

This application is a §371 National Stage Application of PCT/EP2009/050285 filed Jan. 13, 2009, which claims priority to European Application 08151152.9 filed Feb. 7, 2008

BACKGROUND OF THE INVENTION

1 Field of Invention

The invention relates to a method and a device for processing a biological sample. Processing within the sense of the present invention comprises binding, washing and eluting biomolecules of the biological sample.

2 Description of Related Art

Processing of biological materials is used, for example, in the field of extracting and/or purifying biomolecules such as nucleic acids or proteins. For example, a widely known method of purifying the biomolecules is based on the steps of making the contents of a biological sample accessible ("lysis"), selectively binding the constituents of the contents of the biological sample to or on a solid support or carrier material ("binding"), eliminating unwanted constituents from the solid support or carrier material ("washing") and dissolving the desired constituent ("eluting").

In order to permit a desired absorption or desorption of the biomolecules during the purification of the biomolecules, special filter elements have been developed which are formed, for example, from silica gel, and which are, on the one hand, porous or matrix-like, in order to let a liquid pass through the filter element, and which, on the other hand, have a surface to which the biomolecules bind in a specific or unspecific process. In other purification methods, biomolecules are retained on the filter elements simply due to the size exclusion effect. If a liquid containing a biomolecule, such as a nucleic acid, passes the filter element, the biomolecules or a part thereof remain in the filter element in any case, whereas the rest passes through the filter element. Furthermore, in order to obtain the biomolecule from the filter element, an eluting liquid, e.g. nuclease-free water, is brought onto the filter element for desorbing the biomolecule. In this manner, the desired biomolecule is dissolved from the filter element (eluted) and collected in a vessel. Such filter elements are frequently designed as membranes, which are either disposed in individual vessels having an inlet opening and an outlet opening, or which are disposed in multiwell plates. The filter elements are processed either with centrifuges ("spin format") or with apparatuses based on vacuum technology. Individual vessels with an inlet opening and an outlet opening which have a membrane and which can be used in a centrifuge are also known as columns, centrifuging columns, filtering vessels, chromatography columns, "columns", "spin columns" or "single spin columns".

Generally, the advantages of the centrifuging method compared with the vacuum-based methods include a higher degree of purity, a higher concentration and a lower risk of cross contamination. Generally, the best results for the purification of the biomolecules with regard to quality and concentration can be obtained with the centrifuging columns (single spin columns), which are processed under a field of high gravity (>10,000×g), because a minimum cross contamination and a maximum recovery of the desired substance in eluting liquid from the membrane is possible. One drawback, however, is the labor-intensive manual treatment of the centrifuging columns, which increases the risk of error and the processing time, in particular if different samples are to be treated or processed simultaneously. A higher degree of standardization and automation, as well as a higher throughput can be achieved by using multiwell plate formats.

The company QIAGEN GmbH, from Hilden, Germany, offers a broad spectrum of purification protocols and products required therefor for different biomolecules from a multitude of biological samples based on the basic principle of the "bind-wash-elute" protocol. The product "QIAGEN QIAprep Spin Miniprep Kit", for example, is commercially available. For this purpose, different filter materials and devices are used, such as are described, for example, in WO 03/040364 or U.S. Pat. No. 6,277,648.

It is thus known to use a vessel for processing a sample that is open towards the top and sealable. A membrane as a filter element is located at the bottom of the vessel. An opening in the form of a port, which is connected, for example, to a tube, is located under the membrane. Liquid can be withdrawn from the vessel via this tube.

For processing, the biological sample is put into the vessel at the top. Then, the solution which is respectively provided is added, that is, for example, first a lysis buffer in order to disrupt the sample. When the sample has been disrupted, the lysis buffer is withdrawn from the vessel in a downward direction. The lysate contains chemical/physical conditions causing the nucleic acid to bind to the carrier material. The disrupted sample (lysate) is then washed and eluted.

After the nucleic acid of the disrupted sample was bound or adsorbed to the membrane, washing buffers are put into the vessel from the top and withdrawn in a downward direction from the vessel or centrifuged. The washing buffer maintains this binding while simultaneously washing unwanted cellular constituents from the membrane.

As a rule, washing buffers contain ethanol. Ethanol causes nucleic acid to bind to a membrane acting as a filter element. A membrane acting as a filter has a certain dead volume of, for example, 40 µl. It can therefore not be avoided that a corresponding amount of ethanol always remains in the filter. On the one hand, ethanol undesirably contributes to binding. On the other hand, ethanol can also corrupt the results of a later analysis. In order to be able to remove the nucleic acid from the vessel in a downward direction and to avoid faulty analysis results, ethanol is removed first by centrifuging the vessel. The ethanol thus escapes from the membrane and can be removed in a downward direction. Subsequently, the membrane is sufficiently free from ethanol. Ethanol can alternatively be removed from the membrane by means of vacuum and the supply of heat.

Elution is carried out in order to dissolve the nucleic acid from the membrane again. As a rule, this is done using water or a weakly saline, aqueous, pH-stabilized solution. Subsequent to the elution, the nucleic acid can be removed from the vessel in a downward direction through the membrane.

What is problematic in this prior art is that the vessel or a device comprising this vessel has to be opened time and again, as can be seen from the publication "QIAamp® DNA Mini and Blood Mini Handbook, Second Edition, November 2007 (see http://www1.qiagen.com/HB/QIAampDNAMini-AndDNABloodMiniKit_EN). Thus, the sample can escape to the outside. There is a risk of an unwanted contamination.

However, the disruption of a biological sample is carried out in a second vessel better suited to this purpose, in order thus to be able to carry out a disruption particularly effectively. When the biological sample has been disrupted in a second vessel, then it is subsequently filled into the vessel comprising the filter element, that is, a column, and processed. The risk of contamination is increased further by the transfer.

There are various publications regarding the topic of the processing of biological materials. For example, U.S. Pat. No. 6,060,022 discloses an automated system for sample processing comprising an automated centrifuging apparatus. U.S. Pat. No. 5,166,889 describes a collecting system for blood in which a plurality of collecting vessels is positioned in a carrier wheel for direct access. U.S. 2004/0002415 describes an automated centrifuging system for automatically centrifuging liquids containing biological material, such as nucleic acid, in a general centrifuge. WO 2005/019836 describes an apparatus for processing liquid samples. WO 00138046 describes an automated device for charging a centrifuge, in which columns are provided to the centrifuge via an automated routing system. EP 122772 describes a chemical manipulator for use with reaction vessels. GB 2 235 639 describes a centrifuge with a protective casing surrounding the rotating bowl shell. According to WO 2006/042838 A1, a single-use cartridge is proposed which comprises a system of micro-channels and micro-cavities for a predetermined process after the sample has been accommodated. An apparatus for processing biological material is known from DE 10 2006 027 680 A1. DE 102005053463 A1 discloses a reaction unit comprising a bottom part and a top part, for pipetting liquids, wherein the bottom part consists of a reaction cavity with a permeable filter mesh insert and the top part constitutes a reaction cavity that can be affixed to the bottom part and contains a recess or sleeve for accommodating a magnet. Nucleic acids are bound to magnetic particles. Devices for automatically processing known from the prior art often are disadvantageous in that a technically complex apparatus has to be used. The device known from U.S. 2006/0281094 is an example for a technically complex apparatus. Such devices are relatively expensive and require a relatively large amount of space. It is not possible to integrate such a complex and large apparatus into microfluidic systems, such as those known from WO 2006/042838 A1.

Microfluidic systems are advantageous for the integration of complex processes in closed systems (lysis, sample preparation, amplification, detection). This demand for closed systems arises in the field of diagnostics, in which cross contamination has to be avoided. Cross contaminations can be particularly serious if very sensitive detection methods (e.g. PCR—polymerase chain reaction, that is, a method in which minute amounts of a DNA portion can be multiplied in a chain reaction) are used. Moreover, operating errors are avoided by the integration of the procedures.

A microfluidic system for handling and/or detecting particles such as cells or glass beads is known from document U.S. 2004/0229349. According to the fifth example disclosed in this document, a microfluidic system comprises a feeding channel and a waste channel, which are interconnected via filter channels. Particles get into the filter channels via the feeding channel. The particles, for example erythrocytes, are retained by filters located in the filter channels. However, liquids can still get into the waste channel from the feeding channel via the filter channels. By reversing the direction of flow of the liquid through the filter channels, as well as after the suitable actuation of valves, the particles are finally transported out of the filter channels into an analysis zone. It is not known from U.S. 2004/0229349 to feed buffers used for processing into the vessel with a biological sample contained therein via an inlet or outlet through a filter of a vessel.

In order to increase sensitivity alternatively or additionally to PCR, large sample volumes can be prepared. The preparation of large volumes, however, is contradictory to the demand for microfluidic systems for automatic lysis, processing and/or analysis of biological samples. There is therefore a demand for solutions which permit preparing a large sample volume by means of, for example, filtration, and to make the isolated nucleic acids available in a small volume to a microfluidic system via a microfluidic interface. Such a microfluidic interface for membrane-based preparation methods is not known. As a rule, this problem is solved in integrated microsystems by means of bead-based purification processes.

An extraction device with a filter unit for automatically carrying out the processing (binding-washing-eluting) of nucleic acids is known from EP 1382675 A1. In this case, a sample that has been previously lysed is put on the filter unit by the user. Passing the sample through the filter membrane can be carried out by means of a vacuum. Subsequent washing solutions are automatically added and sucked over the membrane. The elution step takes place in the same way after an elution buffer has been added. For the following reasons, this device is not suitable for connection to a microfluidic system if the vessel volume is supposed to be large.

The "bind-wash-elute" process is always carried out for sample preparation with filter-based spin columns. In this case, the liquids are put on the membrane only from the top—as is the case, for example, in the device known from EP 1382675 A1—and drained off at the bottom on the outlet (by centrifugation or vacuum). If the volume of the vessel or column is too large to be able to accommodate large quantities of liquid, the latter is expediently configured such that large volumes can easily be fed to it from the top. For elution in small volumes, however, the liquid must be pipetted exactly onto the center of the membrane in order to accomplish an efficient elution. Thus, feeding small quantities of liquid from the top cannot be carried out for a connection to microfluidic systems, or only with difficulties, and is not advantageous in any case.

SUMMARY OF THE INVENTION

It is an object of the invention to provide a method and a device for the automatic processing of biological samples which can have a relatively large volume and which are processed further by a microfluidic system.

DETAILED DESCRIPTION OF A PREFERRED EMBODIMENT

A sealable or sealed vessel provided with a filter is used for accomplishing the object. The filter can consist of a silica gel. A biological sample is introduced into the vessel, and the vessel is preferably sealed. The biological sample can already be disrupted. However, the sample introduced into the vessel may also be disrupted in the vessel only when the processing is being carried out. An inlet or outlet for liquid is provided underneath the filter. In order to carry out the processing, liquids located in the vessel are not only withdrawn through the filter and passed on via the inlet or outlet, but liquids required for processing are also pumped therethrough through the filter into the vessel. Since only one line is required for automated processing, the vessel can be connected to a microfluidic system with relative ease. However, two lines may also be passed through the bottom of the vessel, with one line preferably serving the inlet and another line preferably serving the outlet. However, one line was found to be completely sufficient. The vessel can remain sealed during processing. Contaminations that could otherwise easily occur are thus avoided. Because the vessel can easily be connected to a microfluidic system, the vessel can be relatively large and be connected with the microfluidic system not until this is required for carrying out automated processing. However, the vessel can also be firmly connected with an inlet or outlet of a microfluidic system. In this case, a microfluidic system is a closed system with which a biological sample is prepared and/or analyzed automatically or semi-automatically. The diameters of the channels of the microfluidic system are relatively small and no larger than 1 mm. A microfluidic system within the sense of the invention substantially consists of a flat substrate provided with channels, chambers and valves. The substrate preferably is only a few cm wide and long, for example, maximally 10 cm wide and long, and has, for example, the base surface area of a check card. The substrate can already comprise miniaturized pumps.

In order to be able to process a large volume within the sense of the invention, the volume of the vessel is in particular at least 150 µl, preferably at least 0.5 ml, particularly preferably at least 1 ml. Preferably, the volume of the vessel is maximally 3 ml.

It is possible in many cases to disrupt a biological sample in the vessel with a lysis buffer, that is, a solution. Preferably, the lysis buffer is in that case also fed to the vessel via the inlet or outlet through the filter, in order thus to be able also to carry out the disruption of the cells automatically. If the disruption is completed, the lysis buffer is withdrawn through the filter via the inlet or outlet. Then, a disrupted sample located in the vessel remains, that is, nucleic acid, which as a rule adheres to the filter.

In order to be able to disrupt a biological sample located in the vessel, the sample has to be intensively mixed regularly with a lysis buffer. Otherwise, an effective disruption of a biological sample is not possible. Tests have shown that the required mixing can be carried out successfully by repeated partial withdrawal of the lysis buffer and pumping it back into the vessel through the inlet or outlet. It has proved to be particularly important in this case that the lysis buffer is pumped through the filter in the process. This results in strong turbulences in the vessel, which have proved to be important for effective mixing.

If the biological sample is disrupted in the vessel in which processing is carried out subsequently, then a transfer of the biological sample from one vessel into a second one can be avoided. The risk of contamination is reduced accordingly.

Subsequent to a disruption with a lysis buffer, ethanol is introduced into the vessel in one embodiment of the invention, preferably via the inlet or outlet. At this moment, lysis buffer and the sample are located in the vessel. Though ethanol also additionally contributes to disruption, what is decisive, however, is that the ethanol causes the nucleic acid to bind to the filter in an increased extent. If the lysis buffer and ethanol are completely pumped off via the filter and the inlet or outlet, the nucleic acid of the disrupted sample remains.

The vessel, the filter element or the filter, as well as the feed lines are then free from lysis buffer and ethanol as far as possible. Subsequently, one or more washing buffers are being pumped into the vessel from below. The filter and the disrupted biological sample are thus washed, preferably again by feeding and withdrawing washing buffer several times, so that turbulences are being produced in the vessel. The disrupted sample or nucleic acid is thus purified, and this is done particularly reliably if turbulences are produced in the aforementioned manner. Fats, lipids and proteins are removed by washing.

Then, the washing buffer, or the washing buffer used last, are again withdrawn completely from the vessel and the inlet or outlet.

If there is ethanol in the filter thereafter, then ethanol is first removed. Preferably, ethanol is removed by supplying heat and by generating a vacuum in the vessel, in order to avoid mechanical movements that could damage a microfluidic system connected thereto.

Then, elution liquid, that is, water or weakly saline water, for example, is pumped into the vessel from below through the filter, is preferably withdrawn again, and pumped through again, in order not only to introduce elution liquid into the vessel, but also to produce turbulences. Again, the efficiency of the desorption of the nucleic acids is increased by the turbulences. An increase of the yield can thus be accomplished compared with the prior art, in which the various liquids or solutions are filled into the vessel with a filter element from the top during processing and withdrawn in a downward direction.

Figure 1:
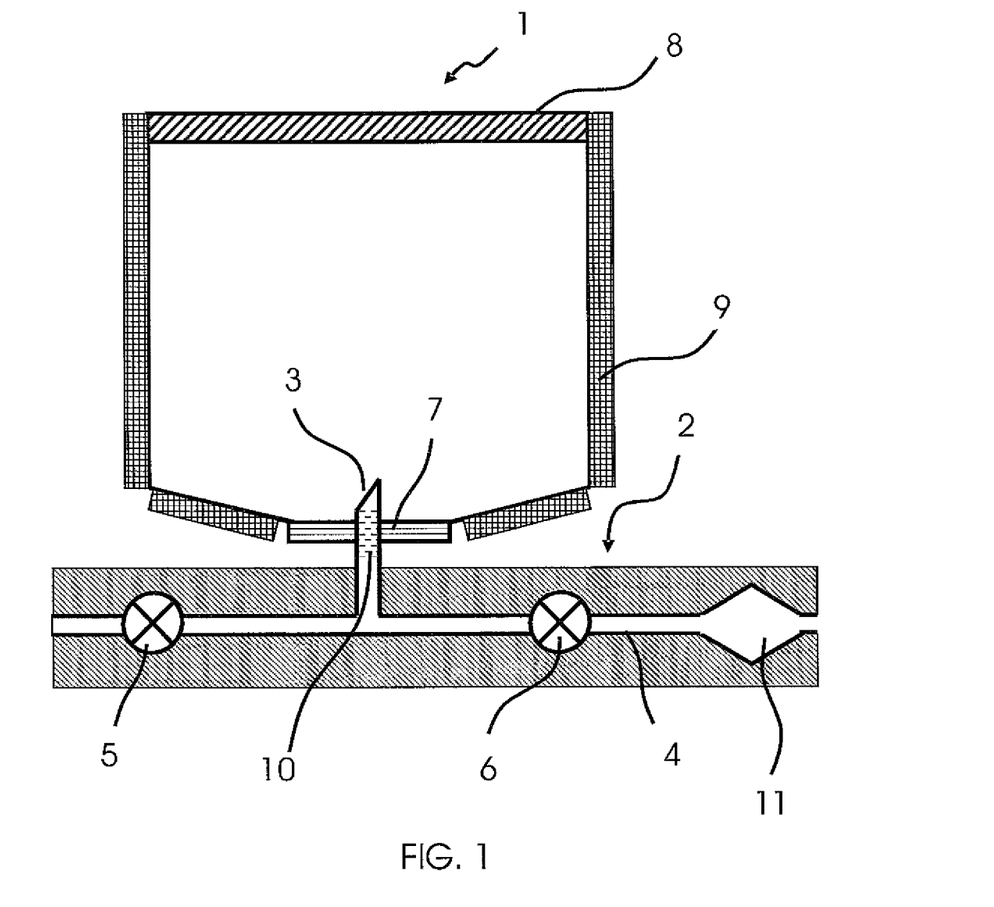
FIG. 1 shows an embodiment of a device for carrying out the method according to the invention.

FIG. 1 shows a first example of a device according to the claims, namely a section through a vessel 1 which is connected to a microfluidic system 2 via an inlet or outlet 3. The inlet and outlet is formed by a hollow needle 3 with a filter 10 located therein. Channels 4 of the microfluidic system and the hollow needle 3 have a diameter of no more than 1 mm. Furthermore, the microfluidic system comprises valves 5 and 6 and/or pumps in order to pump liquid into the vessel 1 in a dosed manner or to be able to withdraw liquid from the vessel. The bottom of the vessel is formed by a rubber membrane 7. The membrane 7 is pierced with the hollow needle 3 and the microfluidic system is thus connected to the vessel 1. On its inside, the hollow needle 3 has a filter membrane 10. Liquid getting from the vessel 1 into the microfluidic system 2 or vice versa is compelled to pass the filter 10.

The vessel 1 comprises a lid 8 with pressure equalization with which the vessel can be sealed again at the top. Pressure equalization is ensured by a semi-permeable, hydrophobic membrane. PTFE membranes (also known as GoreTex membrane) by the company Gore can be used for this purpose. A negative or positive pressure in the vessel that is too large is avoided by the pressure equalization. In the lower region, the vessel tapers towards the membrane 7 in a funnel-shaped manner, in order to be able to withdraw liquid from the vessel in a downward direction as completely as possible. Heating members 9 rest on the outside of the vessel 1.

The upper diameter of the vessel can be a few centimeters, for example, 2 cm. The vessel can be a few centimeters in height, for example, 2.5 cm. The volume of the vessel can be a few ml, for example, 800 µl to 5 ml. A spin column, for example by the company Qiagen, from Hilden, Germany, can be used as a vessel. A glass fiber cloth having a pore size of, for example, 0.7 µm to 4 µm can be used as a filter. The vessel can consist of a plastic material.

In order to carry out the method according to the invention, a sample is first introduced into the vessel 1 from the top. This may be done using a pipette while the lid is open, or via an adapter present in the lid, for example a Luer adapter. However, the lid 8 can also be pierced with a needle in order thus to introduce a biological sample into the vessel. For this purpose, the lid may comprise a rubber septum which is being pierced.

In the example shown in FIG. 1, if a first valve 5 of a connected microfluidic system is opened accordingly, the commercially available QUIAGEN lysis buffer AL, for example, is expediently pumped into the vessel 1 via a first feeding channel and via the inlet or outlet or hollow needle 3 and intensively mixed with the sample by lifting and lowering the liquid level in the vessel 1 by means of pumping and withdrawing. Strong turbulences in the vessel are produced in the process due to the membrane 6. Liquid is withdrawn through the second valve 6 which is at that time temporarily opened and, alternating therewith, liquid is pumped into the vessel through the first valve 5, which is open in due time.

Then, ethanol as a binding mediator, for example, is pumped through the valve 5 into the vessel 1. The lysate is thus mixed with the ethanol (EtOH).

After mixing the lysate with the ethanol, the valve 5 is closed, the valve 6 is opened and a negative pressure is generated in the channel with the valve 6. The lysate is thus pulled through the filter 10. The liquid is thus withdrawn from the vessel 1. Nucleic acids are bound to the filter 10 in the process.

Then, the commercially available washing buffers AW1 and AW2, for example, are used for washing. The valve 6 is closed and the valve 1 is opened. First, AW2 can be pumped into the vessel. The valve 5 is then closed, the valve 6 is opened and through it, the washing buffer is withdrawn from the vessel 1 again. The washing buffer AW1 is then pumped into the vessel and withdrawn again in the same manner. The order of the washing buffers used can be changed.

After the washing buffers have been pumped off completely through the valve 6, the vessel 1 is heated using the heating members 9 and the heated air is pumped off through the opened valve 6. Ethanol is practically completely removed, especially from the filter. Heating to 60° C. is sufficient. If the volume of the vessel is 1 ml, then 500 μl are in each case sufficient, as a rule, for carrying out the method.

After closing the valve 6 and opening the valve 5, 50 μl, for example, of the commercially available elution buffer AVE is pumped through the opened valve 5 into the vessel 1. By actuating the valves 5 and 6 and by pumping and withdrawing accordingly, the elution buffer is conducted past the filter 10 several times.

In one embodiment of the invention, the elution buffer can advantageously be pumped into a PCR chamber 11 of the microfluidic system in order to dissolve dried PCR reagents located therein, in order thus to carry out a PCR quickly and simply. The volume of the PCR is typically 50-100 μl, and is thus considerably smaller than the volume of the vessel 1.

Advantageously, it is possible in the embodiment shown in FIG. 1 to manufacture and store the vessel 1 separately from the microfluidic system and connect them with each other just before the preparation of a biological sample is carried out. It is not imperative that a lid 8 is provided in this embodiment. Instead, the membrane closure 7 can seal an opening via which the vessel 1 is filled with a biological sample. A means for effecting a pressure equalization can, for example, be provided laterally, instead of in the region of the lid 8. Means for providing a pressure equalization in the vessel 1 are, however, not an absolute requirement, especially not if the vessel is always only partially filled with liquid.

However, it is also possible to provide a firm connection, for example a screwed connection between the vessel 1 and the microfluidic system 2. In that case, configuring the inlet or outlet as a protruding hollow needle is unnecessary. A normal tube or channel is sufficient.

For proving the feasibility, genomic DNA was prepared from 200 μl CPDA blood (blood bag) using the commercially available QIAamp Micro Kit by QIAGEN from Hilden, Germany. The method according to the invention was carried out as follows.

The QIAamp MinElute Spin Column was pushed onto a Luer three-way stopcock and served as a vessel within the sense of the present invention.

20 μl proteinase K and 200 μl blood were filled into the column from the "top".

200 μl buffer AL were fed into the column from "below" through a channel of the Luer stopcock.

By moving the syringe plunger of an attached 1 ml syringe back and forth, the liquids were mixed within the column and in the syringe.

The contents of the column were now transferred into an Eppendorf tube and incubated at 56° C. for 15 min. Alternatively, this incubation step can also be carried out in the column by sealing the column with a female Luer stopper and incubating it in an Eppendorf thermomixer (held by the "collection micro-tube", contained in the kit). In this case, the heat input must be optimized due to the double wall. It was shown in principle that this variant of the protocol also works.

After incubating and returning the lysate into the spin column, 200 μl ethanol was fed to the column from below via the Luer stopcock.

By moving the syringe plunger, the liquids were mixed within the column and in the syringe.

The contents of the column were now withdrawn by means of a large-volume syringe. The DNA is bound to the silica membrane in the process.

500 μl washing buffer AW1 is now fed into the column from below with a syringe, and the membrane is washed by moving the syringe plunger back and forth. The contents of the column were now withdrawn by means of a large-volume syringe.

The preceding step is repeated with the washing buffer AW2.

After the washing buffer has been removed, the membrane is dried from below under a vacuum (4 min at −800 mbar).

The DNA is now eluted with 50 μl buffer AE. For this purpose, the volume is fed by means of a 1 ml syringe, and the DNA is eluted from the membrane by moving the syringe plunger back and forth for 30 sec. The entire eluate is sucked back into the syringe and transferred into the 1.5 ml reaction vessel microtube in order to be able to carry out quantitative and qualitative analyses manually.

In the case of reference samples, the protocol was carried out in accordance with the specifications described in the QIAamp Blood Mini Kit Handbook by Qiagen from Hilden, Germany.

Figure 2:
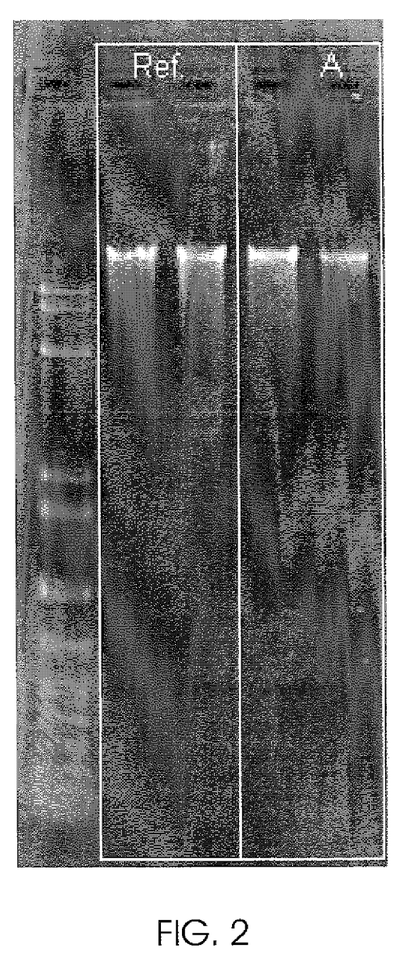
FIG. 2, which relates to agarose gel, shows the analysis data of the tests described herein.

After preparation, the nucleic acids were electrophoretically separated on an agarose gel. After separation, the nucleic acid fragments were colored in an ethidium bromide-containing water bath, caused to light up on a UV light panel and photographed by means of a photodocumentation system. The genomic DNA can be discerned as a bright band in the upper third of the FIG. 2*a*.

Figure 3A:
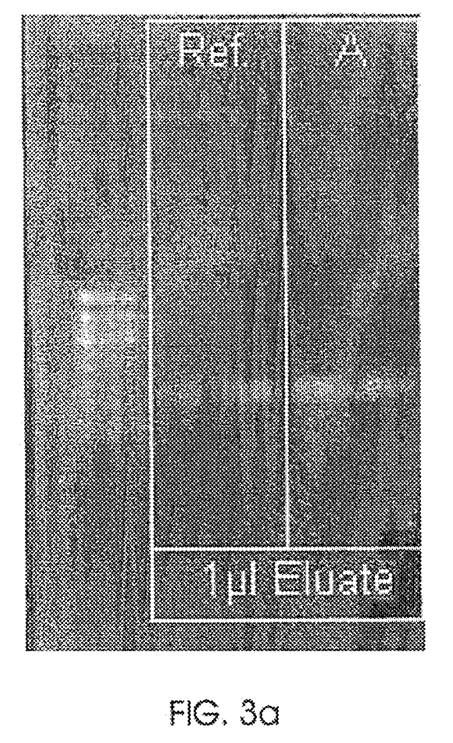
FIG. 3, which relates to agarose gel after PCR, shows the analysis data of the tests described herein.
Figure 3B:
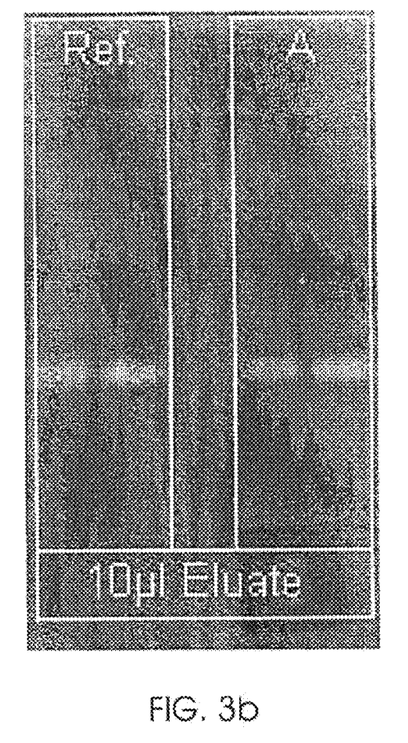

FIGS. 2 and 3a and 3b show the analysis data of the tests described. FIG. 2 relates to agarose gel. The strength, in other words, the light intensity (number and surface area of white pixels) of a band in FIG. 2 is a measure for the quantity. The position and clarity of the bands is a measure for the quality. The gel confirms that comparable concentrations are obtained independent from whether one proceeds according to the handbook known from the prior art, or in accordance with the method according to the claims.

FIGS. 3a and 3b relate to agarose gel after PCR. The bands in the column "Ref." relate to the comparative tests carried out in accordance with the prior art. The bands in the column "A" relate to the tests carried out according to the invention. Different volumes of eluate were put into a PCR, namely 1 μl eluate (FIGS. 3a) and 10 μl eluate (FIG. 3b), and were then separated on an agarose gel. The bands in the center of the image (seen vertically) show the amplified nucleic acid. Practically no differences were found between a band obtained in a comparative test and a band obtained according to the invention. It follows therefore, firstly, that the nucleic acids obtained can be successfully used for a PCR reaction. Secondly, the success with 10 μl eluate input volume shows that the quality of the nucleic acid has no inhibitory effect on the PCR. Depending on the preparation method, it may happen that PCR does not work with 10 μl eluate input volume, because inhibitory molecules are present as contaminants in the eluate, causing drastic effects in the case of increased eluate input volume in the PCR.

The tests performed thus show that a way of conducting the liquids in spin columns modified according to the invention as compared with the prior art is possible without having to accept drawbacks with regard to the results obtained. The modified way of conducting the liquids in spin columns opens up new possibilities with regard to implementing membrane technology for purifying nucleic acids in a microfluidic environment.

Figure 4:
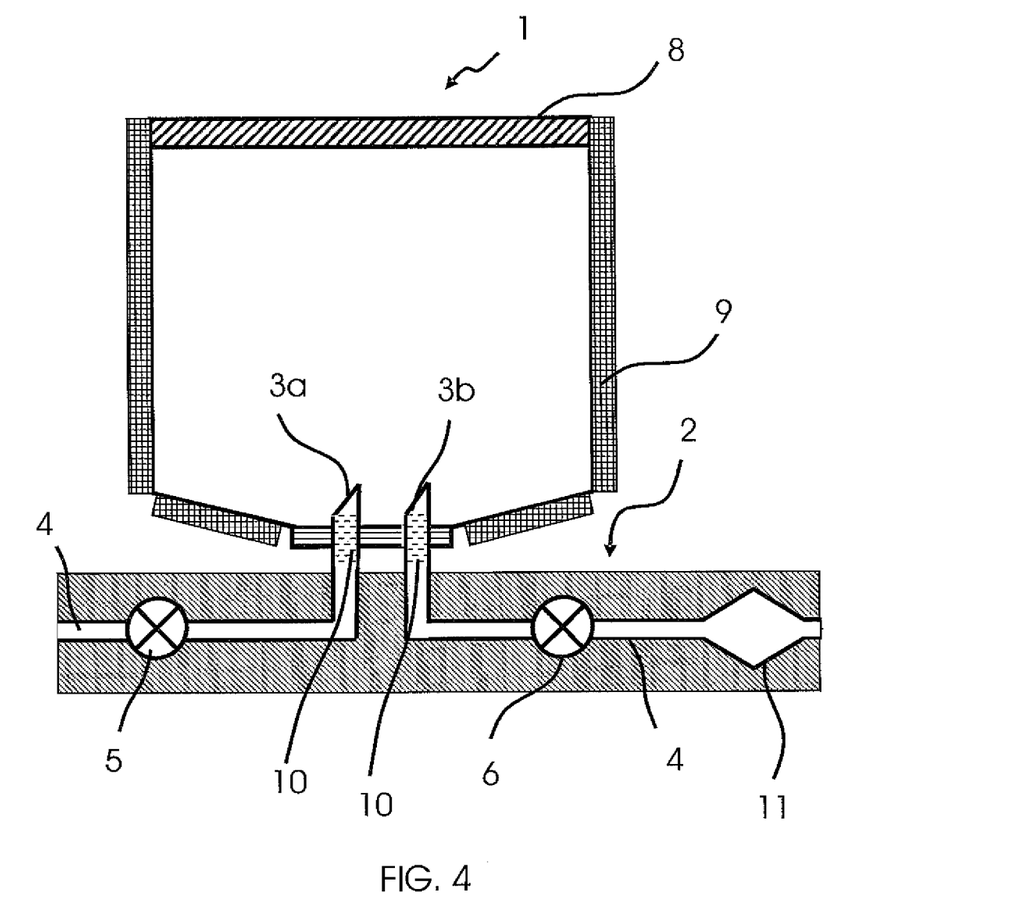
FIG. 4 shows an embodiment with an inlet and an outlet, each of which is configured as a hollow needle.

FIG. 4 shows an alternative embodiment with an inlet 3a and an outlet 3b, each of which are configured as a hollow needle. The inlet and the outlet are close to each other. In this embodiment, it is therefore very easily possible to connect the relatively large vessel (1) with a microfluidic system in order thus to provide a large volume of a vessel. The volume of the vessel is large in particular if it is at least twice the size, preferably at least three times the size of the volume of the largest chamber integrated in the microfluidic system. Thus, the volume of the vessel 1, for example, is in that case at least twice the size, preferably at least three times the size of the volume of the PCR chamber 11 shown.

It is clear from FIG. 4 that it is not an absolute requirement to use the same filter for the inlet and outlet. It is not even absolutely necessary that the inlet has a filter in order to connect the relatively large vessel (1) with a microfluidic system in a suitable manner. However, this is in that case a poorer embodiment of the invention because the generation of desired turbulences is more difficult.

Membranes consisting of other elastic materials can also be used instead of rubber membranes. What is of special importance is merely that such a membrane can be pierced by a needle, and that the needle is connected with the membrane in an externally liquid-tight manner. If a membrane can be expanded elastically, it is capable of providing for pressure equalization. This is of importance especially for a relatively large-surface membrane limiting the vessel towards the top.

Figure 5:
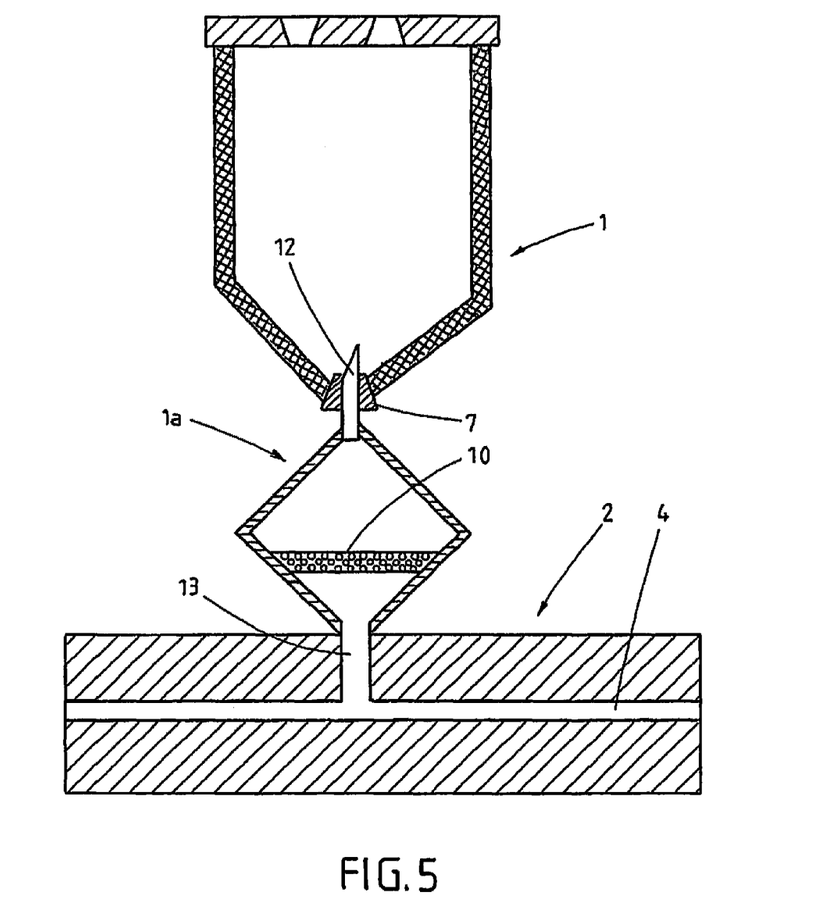
FIG. 5 shows an embodiment of a device for carrying out the method according to the invention.

FIG. 5 shows another example of a device for carrying out the method according to the invention. A chamber 1a is firmly connected to a microfluidic system 2. Preferably, the chamber 1a is relatively small compared with an associated vessel 1. In particular, the volume of the vessel 1 is at least twice the volume of the chamber 1a. A filter 10 is located in the chamber 1a. Underneath the filter 10, there is an inlet or outlet 13 via which the liquid can be conducted from the microfluidic system 2 into the chamber 1a and vice versa. The chamber 1a has a hollow needle 12 above the filter 10, with which a rubber septum or a membrane 7 of the vessel 1 can be pierced in order thus to provide a connection between the chamber 1 a and the vessel 1. Compared to the embodiment shown in FIG. 1, this embodiment is advantageous in that the filter element 10 can easily have a relatively large surface area because the filter element is not located in a thin hollow needle, but in a very much wider vessel. The larger filter surface area has a favorable effect on carrying out the method. This way, more surface area is available for generating turbulences and thus, a good mixing effect. Compared with an embodiment shown in the subsequent FIG. 6, the embodiment shown in FIG. 5 is advantageous in that a vessel or chamber firmly mounted on the microfluidic system can be relatively small. The good handling properties of the microfluidic system are thus less affected by the mounted vessel or the mounted chamber. Otherwise, the embodiment shown in FIG. 5 works in the same way as the embodiment shown in FIG. 1.

Figure 6:
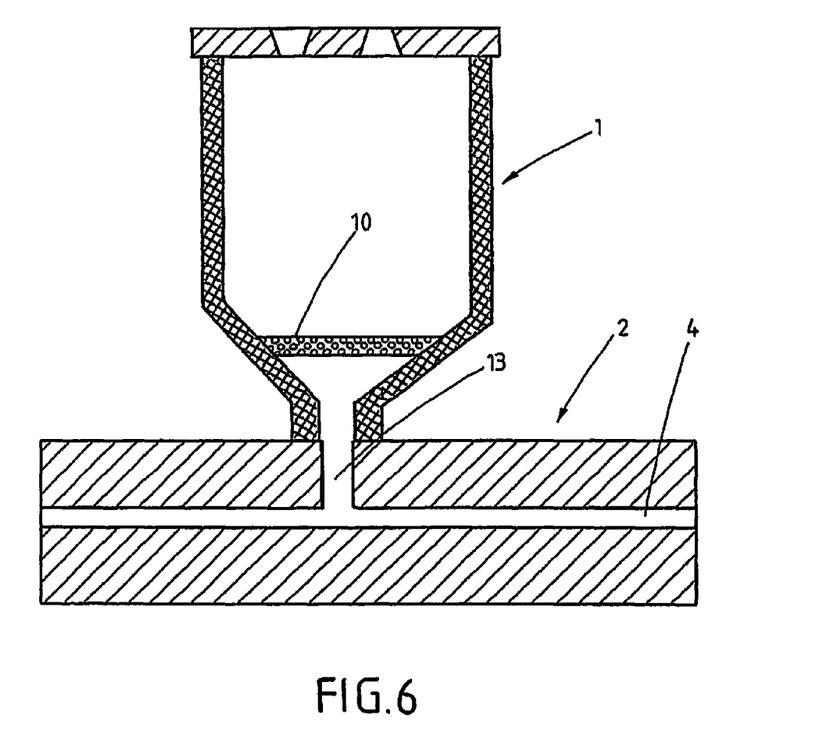
FIG. 6 shows the case in which the vessel is firmly connected to the microfluidic system via an inlet or outlet.

FIG. 6 shows the case in which the vessel 1 is firmly connected to the microfluidic system 2 via an inlet or outlet 13. A relatively large-surface filter element 10 is located in the vessel 1, close to the inlet or outlet 13.

The method according to the claims can also be transferred onto proteins.

The invention claimed is:

1. A method for processing a biological sample, the method comprising:
    flowing a buffer in an inlet/outlet line through a filter and into contact with the biological sample contained in a vessel, the vessel being coupled to the inlet/outlet line; wherein the vessel comprises a membrane and the inlet/outlet line comprises a needle, and further comprising, prior to the flowing, piercing the membrane to couple the vessel to the inlet/outlet line; and
    removing the buffer from the vessel by flowing through the filter and through said inlet/outlet line.

2. The method according to claim 1, wherein said buffer is pumped into the vessel via a microfluidic system and are withdrawn from the vessel via the microfluidic system.

3. The method according to claim 2, wherein the diameters of channels of the microfluidic system are no larger than 1 mm.

4. The method according to claim 1, wherein the filling volume of the vessel is at least 150 μl.

5. The method according to claim 1, wherein said buffer comprises a lysis buffer for disrupting the biological sample located in the vessel is pumped through the filter into the vessel.

6. The method according to claim 1, wherein the liquid level of a buffer located in the vessel is lifted and lowered several times by the buffer being partially pumped through the filter into the vessel and partially withdrawn therethrough.

7. The method according to claim 1, wherein said buffer comprising ethanol through the filter into the vessel with a disrupted sample located therein, and is subsequently withdrawn from the vessel via the filter.

8. The method according to claim 1, wherein said buffer comprising a washing buffer is pumped through the filter into the vessel with a disrupted sample located therein, and is subsequently withdrawn from the vessel via the filter.

9. The method according to claim 1, wherein ethanol is removed from the vessel by heating the vessel and/or withdrawing said ethanol from the vessel.

10. The method according to claim 1, wherein said buffer comprising an elution liquid is pumped through the filter into the vessel with a disrupted sample located therein, and said elution liquid is subsequently withdrawn from the vessel via the filter.

11. The method according to claim 1, wherein the vessel is connected with a microfluidic system via a hollow needle.

12. The method according to claim 1, comprising coupling the vessel to a microfluidic system via said inlet/outlet line, wherein the flowing and the removing are performed using the microfluidic system.

13. The method according to claim 1, wherein the filter is disposed in a portion of the inlet/outlet line.

14. The method according to claim 1, wherein the filter is disposed in a chamber between the inlet/outlet line and the vessel.

15. The method according to claim 1, wherein the filter is disposed in a portion of the vessel between the biological sample and the inlet/outlet line.

16. The method according to claim 1, wherein the filter is constructed to retain portions of the biological sample therein and to release the retained portions in response to an eluting agent passing through said filter.

17. The method according to claim 1, wherein the flowing and the removing are repeated such that a turbulent flow is induced in said vessel to mix the biological sample with the buffer.

* * * * *